(12) United States Patent
Gassler et al.

(10) Patent No.: US 10,485,451 B2
(45) Date of Patent: Nov. 26, 2019

(54) TRACKING A DENTAL MOVEMENT

(71) Applicant: FORSTGARTEN INTERNATIONAL HOLDING GMBH, St. Gallen (CH)

(72) Inventors: Guido Gassler, Ulm (DE); Stefan Kaltenbach, Rebstein (CH)

(73) Assignee: FORSTGARTEN INTERNATIONAL HOLDING GMBH, St. Gallen (CH)

(*) Notice: Subject to any disclaimer, the term of this patent is extended or adjusted under 35 U.S.C. 154(b) by 0 days.

(21) Appl. No.: 15/555,997

(22) PCT Filed: Mar. 3, 2016

(86) PCT No.: PCT/EP2016/054333
§ 371 (c)(1),
(2) Date: Sep. 6, 2017

(87) PCT Pub. No.: WO2016/142264
PCT Pub. Date: Sep. 15, 2016

(65) Prior Publication Data
US 2018/0055420 A1   Mar. 1, 2018

(30) Foreign Application Priority Data
Mar. 6, 2015 (EP) ..................... 15157970

(51) Int. Cl.
*A61B 5/11* (2006.01)
*A61C 19/045* (2006.01)
(Continued)

(52) U.S. Cl.
CPC ........... *A61B 5/1111* (2013.01); *A61B 5/0002* (2013.01); *A61B 5/4542* (2013.01);
(Continued)

(58) Field of Classification Search
CPC ... A61B 5/1111; A61B 5/0002; A61B 5/4542; A61C 19/045; A61C 19/052; A61C 7/002
(Continued)

(56) References Cited

U.S. PATENT DOCUMENTS 9,004,917 B2 * 4/2015 Brunner ............... A61C 19/045
433/69
2004/0157188 A1 * 8/2004 Luth ....................... A61B 34/20
433/75
(Continued)

FOREIGN PATENT DOCUMENTS

DE   20 2013 001383   3/2013
DE   10 2012 003929   9/2013
(Continued)

OTHER PUBLICATIONS

The International Search Report (ISR) for PCT/EP2016/054533 dated Apr. 27, 2016, pp. 1-4.
(Continued)

*Primary Examiner* — Matthew M Nelson
(74) *Attorney, Agent, or Firm* — McDonnell Boehnen Hulbert & Berghoff LLP

(57) ABSTRACT

It is described an arrangement (230, 330, 430, 530) and a method for tracking a movement of an upper jaw (100) relative to a lower jaw (120), the arrangement comprising: a lower mounting structure (231) mountable relative to the lower jaw (120); at least one lower motion sensor system (233) mounted at the lower mounting structure; and at least one data transmission unit (127) adapted to transmit measurement data (245) from the lower motion sensor system to an analysis unit (239).

22 Claims, 4 Drawing Sheets

(51) Int. Cl.
  *A61C 19/05* (2006.01)
  *A61B 5/00* (2006.01)
  *A61C 7/00* (2006.01)

(52) U.S. Cl.
  CPC .......... *A61C 19/045* (2013.01); *A61C 19/052* (2013.01); *A61C 7/002* (2013.01)

(58) Field of Classification Search
  USPC .......................................................... 433/68
  See application file for complete search history.

(56) References Cited

U.S. PATENT DOCUMENTS

| | | | | |
|---|---|---|---|---|
| 2005/0163342 | A1* | 7/2005 | Persky | A61B 6/14 382/103 |
| 2007/0190481 | A1* | 8/2007 | Schmitt | A61C 9/0046 433/68 |
| 2010/0151409 | A1* | 6/2010 | Munehiro | A61C 11/00 433/54 |
| 2011/0053110 | A1* | 3/2011 | Bando | A61B 5/1121 433/68 |
| 2012/0107763 | A1* | 5/2012 | Adams | A61B 1/24 433/29 |
| 2013/0122463 | A1* | 5/2013 | Csillag | A61C 8/0089 433/173 |
| 2013/0157218 | A1* | 6/2013 | Brunner | A61C 19/045 433/69 |
| 2013/0253286 | A1* | 9/2013 | Fridman | A61B 5/0402 600/301 |
| 2013/0280671 | A1* | 10/2013 | Brawn | A61N 5/0603 433/24 |
| 2014/0212832 | A1* | 7/2014 | Fisker | A61B 5/0062 433/29 |
| 2014/0288432 | A1* | 9/2014 | Hennig | A63B 71/085 600/476 |
| 2015/0140502 | A1* | 5/2015 | Brawn | A61C 7/08 433/24 |
| 2015/0173856 | A1* | 6/2015 | Lowe | A61C 7/008 433/24 |
| 2015/0196372 | A1* | 7/2015 | Champleboux | A61B 6/14 433/29 |
| 2015/0230880 | A1* | 8/2015 | Feine | A61C 1/0015 433/27 |
| 2016/0343270 | A1* | 11/2016 | Zheng | A46B 15/0002 |

FOREIGN PATENT DOCUMENTS

| | | |
|---|---|---|
| WO | 2011/073436 | 6/2011 |
| WO | 2014/004730 | 1/2014 |
| WO | 2014/050543 | 4/2014 |
| WO | 2014/106519 | 7/2014 |

OTHER PUBLICATIONS

The Written Opinion for the International Searching Authority dated Apr. 27, 2016, pp. 1-5.

* cited by examiner

TRACKING A DENTAL MOVEMENT

CROSS-REFERENCE TO RELATED APPLICATION

This application is a U.S. national phase of International Application No. PCT/EP2016/054533, filed on Mar. 3, 2016, which claims priority to European Patent Application No 15157970.3, filed Mar. 6, 2015, both of which are incorporated by reference herein in their entirety.

The present invention relates to an arrangement and a method for tracking a movement of an upper jaw relative to a lower jaw. Furthermore, the present invention relates to a method for designing and manufacturing a dental supplement for at least one tooth, in particular using the tracking arrangement or tracking method.

BACKGROUND ART

The document WO 2007/085241 A1 discloses a method and device for the recording of body movements, wherein a graphic marker is connected with the body part and an image of the body part comprising the graphic marker is generated by an image recording camera. A processor device determines the position, location and/or movement of the graphic marker in the three-dimensional space, wherein a substantial automation and high measuring precision during the determination of position and movement in the three-dimensional space is achieved without the need of manual calibration of the measurement system. Furthermore, this document discloses a determination of a jaw joint axis and the acquisition of motion trajectories of a lower jaw.

The publication titled "Virtuelle realdynamische Occlusion für Funktionsanalyse and CAD/CAM-Prozesse" von Sebastian Ruge, Diana John, Bernd Kordaβ, in digital_dental.news, 8. Jahrgang, November 2014, pages 6-12 discloses an electronic motion acquisition system for visualizing jaw movements. The document discloses that for digitalizing of teeth surfaces a plaster model is scanned using a 3D scanner. At the lower jaw an ultrasound transmitter equipment is mounted and a receiver microphone is mounted at the skull. During the motion, ultrasound measurements are performed. The three-dimensional position data are visualized and the dentist has the opportunity to detect occlusal problems, such as interferences during the bite or chewing motion.

In the prior art an optical or ultrasound involving measurement method for acquiring position data during a jaw movement have been applied. Thereby, the optical marker is required to be fixed at the upper jaw or the lower jaw using a frame or a strap. Furthermore, it is required to fix the patient, in particular the skull of the patient, using voluminous equipment in order to ensure that the upper jaw is in a fixed position. Thereby, the measurement requires extensive equipment and is inconvenient for the patient.

Thus, there may be a need for an arrangement and a method for tracking a movement of an upper jaw relative to a lower jaw, wherein disadvantages observed in the prior art are reduced or even overcome. In particular, there may be a need for an arrangement and method for tracking a movement of an upper jaw relative to a lower jaw which provides accurate position data to enable reconstructing a motion of the lower jaw relative to the upper jaw during a natural chewing motion. Furthermore, it is desired that such motion data is usable for designing and finally manufacturing a dental supplement to be applied to at least one tooth of the patient.

SUMMARY OF THE INVENTION

The need is satisfied by the subject-matter of the independent claims. The dependent claims specify particular embodiments of the present invention.

According to an embodiment of the present invention an arrangement (for example including hardware and software) for tracking a movement (or at least several distinct states during a movement) of an upper jaw relative to a lower jaw (for example of a patient) is provided. Thereby, the arrangement comprises a lower mounting structure (for example comprising a frame, a bar, a strap, for example comprising an elastic element adapted for clamping onto the lower jaw) which is (fixedly, such that the localization of the lower mounting structure substantially does not change during the movement) mountable relative to the lower jaw. Further, the arrangement comprises at least one (or several, such as two, three, four, five or even more) lower motion sensor system (in particular comprising an actual motion sensor, electronics, storage capability and/or energy supply) mounted at the lower mounting structure, wherein the lower motion sensor system is in particular adapted to detect a change of a positioning due to acceleration and/or rotation. Furthermore, the tracking arrangement comprises at least one (for example exactly one for one or more motion sensor systems or one for each motion sensor system) data transmission unit (in particular for wireless data transmission using electromagnetic waves) adapted to transmit (for example wirelessly or optically or using at least one electric cable) measurement data, such as raw measurement data and/or at least partially processed measurement data, such as to reflect position data as derived for example from acceleration and rotation data from the lower motion sensor system to an analysis unit (for example arranged outside the mouth of the patient, thus representing an external unit).

In the described embodiment only at least one lower motion sensor system may be required to be fixedly attachable to the lower jaw. The skull of the patient and thus the upper jaw may be fixed during tracking the movement, such that by acquiring measurement data from the lower motion sensor system only, the relative movement of the upper jaw and the lower jaw is reconstructable.

The tracking arrangement does not require optical markers or ultrasound transmitters or receivers. Thereby, problems in the prior art where optical markers were obscured may be reduced. The measurement data may for example be transmitted through the skin of the patient, thereby providing higher flexibility for the arrangement/localization of different units of the tracking arrangement. The lower mounting structure may be provided in a number of different configurations in which it may be possible to mount the lower motion sensor system either within the mouth or (partly) outside the mouth of the patient. The lower mounting structure in particular may be adapted to allow mounting the lower motion sensor system without interfering with the movement of the upper jaw and the lower jaw to be analyzed, for example a natural chewing movement.

The at least one lower motion sensor system may be adapted to sample the movement by acquiring measurement data at plural different time instances which may have for example a constant time interval in between. The lower motion sensor system may either transmit the measurement data online during the movement or may be adapted to buffer or store some or all of the measurement data at least temporarily and may transmit the measurement data in portions or in their entirety later, i.e. after the movement is completed. The lower motion sensor system may also store some or all of the measurement data and may only after requesting the measurement data (for example by the analysis unit) transmit the measurement data to the analysis unit.

Thereby, a reliable tracking arrangement may be provided which does not require extensive equipment and may be performed in a convenient manner for a patient.

The tracking arrangement may further comprise an upper mounting structure which may (fixedly) be mountable relative to the upper jaw, for example at the skull of the patient, for example contacting portions of the upper third of the skull, for example supported or contacting portions of the nose and portions of the skull above the ears. The tracking arrangement may further comprise at least one (exactly one or two, three, four or even more) upper motion sensor system (which may in particular be configured similar or even identically to the lower motion sensor system) mounted at the upper mounting structure.

Further, the at least one data transmission unit may further be adapted for transmitting measurement data from the upper motion sensor system to the analysis unit. According to an embodiment of the present invention, to each motion sensor system, i.e. the at least one lower motion sensor system and the at least one upper motion sensor system an individual data transmission unit may be associated. In other embodiments one or more motion sensor systems may utilize a single data transmission unit or at least less than the number of motion sensor system for transmitting measurement data to the analysis unit. For example, all motion sensor systems of the at least one lower motion sensor system may be connected with one data transmission unit which may be adapted to transfer the measurement data of all lower motion sensor systems to the analysis unit. Other configurations are possible.

The data from different motion sensor systems may be transferred using different data transmission technology. In particular, however, all motion sensor systems may transmit the measurement data using the same or a similar transmission technology, in particular involving optical and/or wireless transmission technology, in particular Bluetooth.

When also at least one upper motion sensor system is provided the patient may not be required to be fixed in respect of the upper jaw. Instead, the patient may be allowed to move the skull and thus the upper jaw as well as the lower jaw during acquiring measurement data regarding the movement of the upper jaw relative to the lower jaw. Since the movement of the upper jaw may be tracked or acquired using the at least one upper motion sensor system, the relative motion of the upper jaw relative to the lower jaw may be reconstructed by considering the measurement data acquired by the upper motion sensor system and the measurement data acquired by the lower motion sensor system. Furthermore, an accuracy of the reconstructed relative motion may be improved by using besides the lower motion sensor system the upper motion sensor system.

According to an embodiment of the present invention the lower motion sensor system and/or the upper motion sensor system are configured as position sensors (being capable of detecting a position or at least a position change) with an accuracy of between 0.001 mm and 0.5 mm, in particular between 0.005 mm and 0.3 mm, further in particular between 0.01 mm and 0.2 mm, most particularly between 0.08 mm and 0.12 mm. Thereby, conventionally available position sensors may be employed. Furthermore, the upper motion sensor and/or the lower motion sensor may be configured as micro-electromechanical systems (MEMS). Thereby, the size of the motion sensor systems may be compatible with the usage of reconstructing a jaw movement. For example, the position sensor systems may have a size fitting in a volume of 1 ml or 1 cm×1 cm×0.5 cm, for example.

According to an embodiment of the present invention the upper motion sensor system and/or the lower motion sensor system comprises an accelerometer (capable of detecting or measuring an acceleration, in particular along plural different directions) and/or a gyroscope (capable of detecting and measuring and quantifying rotational movements), in particular a 6-axis or 9-axis combo sensor, such as the Curie Module offered by Intel corporation. The motion sensor system may further comprise a microcontroller, an electronic storage (in particular for storing measurement data, calibration data, operational parameters and the like) and a battery (which may be chargeable from outside). Thereby, a reliable sensor system may be utilized which may be commercially available.

According to an embodiment of the present invention the at least one data transmission unit comprises a wireless data interface, in particular compatible with Bluetooth technology, for transmitting data, in particular measurement data and/or data derived from the measurement data. A wireless data interface has been proven to be very reliable and is furthermore conventionally available. Thereby, the arrangement may be simplified and costs may be reduced.

According to an embodiment of the present invention the upper and/or the lower mounting structure comprises a frame and/or a clamp (comprising elastic elements that may engage body portions of the patients, such as a portion of the skull) and/or a strap (for example an elastic strap), in particular similar to a frame for eye glasses (to be placed onto the nose and partly above the ears of the patient), in particular adapted for para-occlusal mounting, such that a chewing motion is unimpaired while the upper and/or lower mounting structure is mounted at the patient. Thus, the mounting of the motion sensor systems may be achieved in a reliable manner, such as to achieve a fixed positioning of the motion sensor system relative to the upper jaw or the lower jaw, respectively.

The at least one lower motion sensor system and/or the at least one upper motion sensor system may comprise several lower motion sensor systems whose measurement data are combinable for obtaining higher accuracy. The measurement data may be combined by a (common) processor of the motion sensor system or may be combined/processed/averaged at the analysis unit. Thereby, the accuracy and reliability of the tracking system may be improved.

The tracking arrangement may, according to an embodiment of the present invention, further comprise an analysis module (in particular comprising a processor which may further in particular be programmable) for analyzing (for example combining, averaging deriving velocity data from acceleration data, for deriving position data from velocity data) the measurement data acquired during a chewing motion (or during at least several states of a chewing motion or different bite states).

Thereby, the analysis module may comprise an electronic storage for storing a 3D model of the upper jaw including plural upper teeth and the lower jaw including plural lower teeth (the 3D model in particular being obtained by a conventional imprint or other techniques). The analysis module may further be adapted to derive, from the measurement data transmitted from the lower motion sensor system and/or the upper motion sensor system, position data representing positions of the upper teeth/jaw relative to the position of the lower teeth/jaw. The position data may for example represent trajectory data of a trajectory of the lower jaw relative to the upper jaw during the chewing motion. Thereby the position data may be applicable for deriving a jaw movement and/or jaw movement axis.

The analysis module may further be adapted to obtain, from the position data and/or the 3D model, a lower border of a lower volume (the lower border limiting the lower volume) occupied by the lower teeth during the chewing motion and to obtain an upper border of an upper volume (the upper border limiting the upper volume) occupied by the upper teeth during the chewing motion. A volume between the lower border and the upper border may represent a space in which no tooth is present during the entire chewing motion as acquired by the tracking arrangement. To derive such geometry of a void volume (limited by and between the lower border and the upper border) may be helpful in designing a dental supplement for improving a bite situation or chewing motion which may also involve the desire to reposition a chewing axis or lower jaw rotation axis.

According to an embodiment of the present invention the analysis module may further be adapted to define a location and/or geometry of a supplement, in particular a dental supplement, for at least one tooth (in particular to be adhered or applied to at least one tooth) of the lower teeth and/or the upper teeth based on the upper border and the lower border (those borders limiting the void volume which is not occupied by any tooth during the chewing motion). The supplement may be desired to be added to the at least one tooth for achieving a desired bite adjustment or chewing motion. Thereby, a rational methodology for defining the localization and/or geometry of a supplement may be provided.

According to an embodiment of the present invention the analysis module may further be adapted to define a location and/or geometry of an excess portion (which may be desired to be removed) of at least one tooth of the lower teeth and/or the upper teeth based on the upper border and the lower border. The excess portion may interfere with a desired bite adjustment or with a desired chewing motion. The excess portion may be identified at a lateral region where the upper border and the lower border form a common annular edge (or penetrate each other), such that in this lateral region there is no space or no void volume between opposing teeth due to direct contact of portions of opposing teeth.

Where the excess portion is located may be indicated by providing a recognizable feature for the dentist, for example in a computer model of the upper border and the lower border or a computer model of the void volume between the upper border and the lower border. Thereby, a dental treatment by the dentist may conveniently be supported, in order to improve the treatment.

It should be understood that the features which have individually or in any combination been disclosed, described or applied to an arrangement for tracking a movement of an upper jaw relative to a lower jaw may, individually or in any combination, also apply for a method for tracking a movement of an upper jaw relative to a lower jaw according to an embodiment of the present invention and vice versa. According to an embodiment of the present invention it is provided a method for tracking a movement of an upper jaw relative to a lower jaw. Thereby, the method comprises affixing a lower mounting structure relative to the lower jaw, wherein at least one lower motion sensor system is mounted at the lower mounting structure, and transmitting measurement data from the lower motion sensor system to an analysis unit, the measurement data being acquired during a chewing motion.

The method may be performed using an arrangement for tracking a movement as has been explained in one of the embodiments above.

According to still another exemplary embodiment of the invention, a program element is provided, which, when being executed by a processor, is adapted to control or carry out a method for tracking a movement of an upper jaw relative to a lower jaw having the above mentioned features.

According to yet another exemplary embodiment of the invention, a computer-readable medium is provided, in which a computer program is stored which, when being executed by a processor, is adapted to control or carry out a method for tracking a movement of an upper jaw relative to a lower jaw having the above mentioned features.

The tracking method may further comprise repositioning or positioning and/or orienting the lower jaw and the upper jaw to be in a reference relative position/orientation before or after acquiring the measurement data during the chewing motion. Since the motion sensor system or systems may only detect changes of the position, a known reference relative position/orientation may be required to appropriately reconstruct from the measurement data the motion of the upper jaw relative to the lower jaw. The reference position may for example be a state, wherein the upper jaw and the lower jaw firmly contact each other during a bite state. Alternatively, the reference position may be a state, while the patient has his or her mouth (wide) open.

According to an embodiment of the present invention it is provided a method for designing a (dental) supplement for at least one tooth. The designing method comprises performing a method for tracking a movement of an upper jaw relative to a lower jaw as is described in one of the embodiments above. Further, the designing method comprises deriving, from the measurement data, position data representing positions of the upper teeth/jaw relative to positions of the lower teeth/jaw and determining, from the position data and a 3D model of the upper jaw and the lower jaw, a lower border of a lower volume occupied by the lower teeth during the chewing motion and determining an upper border of an upper volume occupied by the upper teeth during the chewing motion. Further, the designing method comprises defining a location and/or geometry of the supplement based on the lower border and the upper border.

Furthermore, a method for manufacturing a supplement for at least one tooth is provided which comprises performing a method for designing the supplement for the at least one tooth according to an embodiment as described above and manufacturing, in particular using a 3D printer, the supplement according to the defined geometry of the supplement.

The defined geometry may be supplied to the 3D printer and the 3D printer may be supplied with plastic material, composite material and/or fiber material as the material for manufacturing the dental supplement.

Embodiments of the present invention are now described with reference to the accompanying drawings. The invention is not restricted to the illustrated or described embodiments.

DETAILED DESCRIPTION OF EMBODIMENTS

Embodiments of the present invention are now described with reference to the accompanying drawings. Thereby, it should be noted that structures or features similar in structure and/or function are designated with reference signs differing only in the first digit. A description of one particular feature or structure not described in detail in a particular embodiment may be taken from the description of this structure or feature in another embodiment illustrated in another figure.

Figure 1:
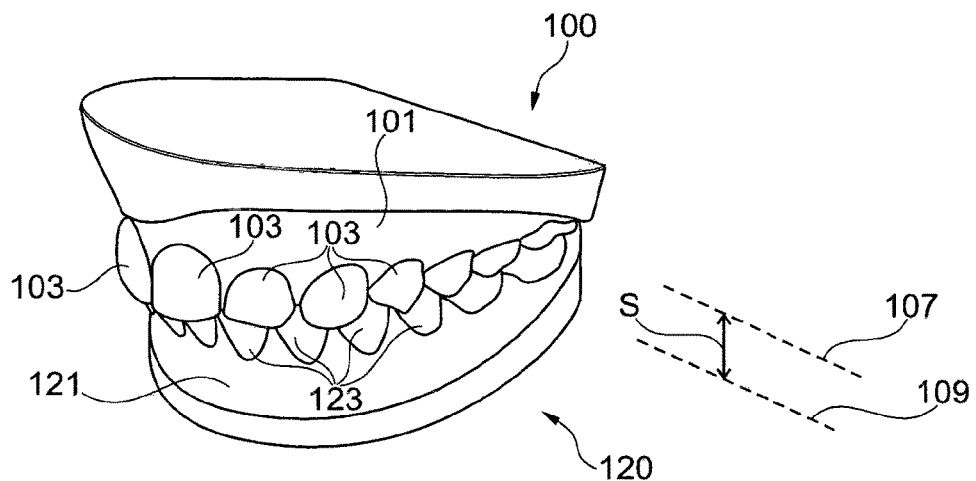
FIG. 1 schematically illustrates a perspective illustration of an upper jaw and a lower jaw in a reference state for a method for tracking a movement according to an embodiment of the present invention.

FIG. 1 schematically illustrates in a perspective view an upper jaw 100 and a lower jaw 120, the upper jaw 100 including an upper teethridge 101 and plural upper teeth 103, the lower jaw 120 including a lower teethridge 121 and plural lower teeth 123. The upper jaw 100 and the lower jaw 120 may belong to a patient to be examined by a dentist with respect for tracking a movement of the upper jaw 100 relative to the lower jaw 120, as carried out according to embodiments of the present invention. For tracking the movement of the upper jaw 100 relative to the lower jaw 120 the upper jaw and/or lower jaw may carry or may have fixed equipment, such as illustrated in FIG. 2, 3, 4 or 5, wherein particular method steps for tracking the movement, designing a supplement and/or manufacturing the supplement are additionally illustrated in FIGS. 6A to 6E, 7A, 7B, 8A, 8B and 9.

Figure 2:
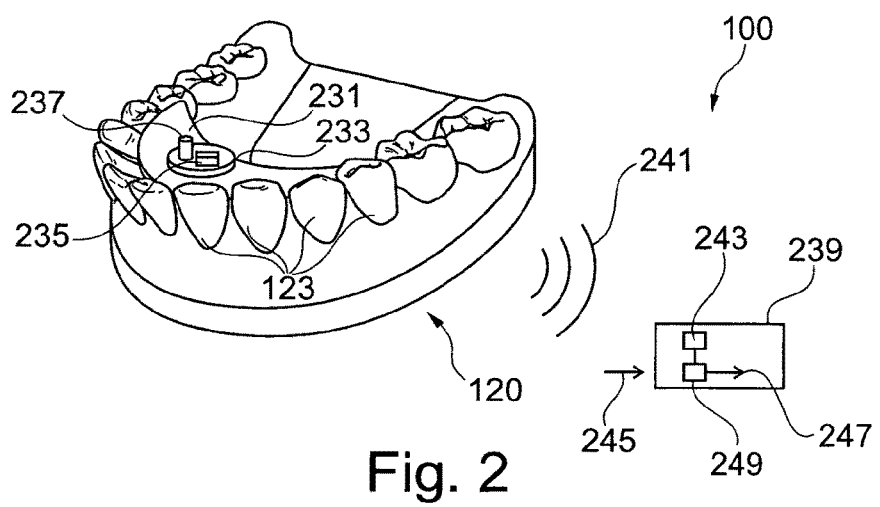
FIG. 2 schematically illustrates a lower motion sensor system installed in a lower jaw as comprised in an arrangement for tracking a movement according to an embodiment of the present invention.

The arrangement 230 for tracking a movement of the upper jaw 100 and the lower jaw 120 illustrated in FIG. 2 comprises a lower mounting structure 231 which is fixedly mountable and hereby mounted relative to the lower jaw 120 in that it is clamped between some of the lower teeth 123. Thereby, the lower mounting structure 231 is formed by an elastic, bendable sheet-like or plate-like structure that may, due to elastic forces or spring forces, engage with inner sections or inner surfaces of the lower tooth 123.

The arrangement 230 further comprises a lower motion sensor system 233 which is mounted (for example adhered to or screwed to) the lower mounting structure 231. The lower mounting sensor system 233 thereby comprises a position sensor 235 which is adapted to detect and measure acceleration and/or velocity and/or position derived therefrom and further comprises a data transmission unit 237 for transmission of measurement data 245 as obtained by the position sensor 235 to an analysis module 239 via electromagnetic waves 241 which are configured or modulated according to Bluetooth transmission technology. The lower motion sensor 233 in the arrangement 230 for tracking the movement is arranged between and/or somewhat below lower teeth 123 within a tongue area.

After having installed the lower motion sensor 233 using the lower mounting structure 231, such as to fix the lower motion sensor 233 in a fixed state relative to the lower jaw 120, the patient may be asked to adopt a reference state, such as a state as illustrated in FIG. 1. In the reference state the upper jaw and the lower jaw 100, 120 press, via the teeth 103, 123 firmly against each other, as for example in a usual bite state. The patient may then be asked to start a motion of the lower jaw relative to the upper jaw, for example to start a normal or natural chewing motion. During the chewing motion the lower motion sensor system 233 detects position, changes of the position, acceleration and/or velocity and/or rotation of the lower jaw 120, while the upper jaw 100 is kept in a fixed position by not illustrated equipment. The measurement data 245 detected by the lower motion sensor system 233 are then, online or after temporarily buffering, transmitted via the electromagnetic waves 241 to the analysis unit 239.

The analysis module 239 may for example comprise an electronic storage 243 where a 3D model of the upper jaw 100 and the lower jaw 120 is stored in an electronic format. The measurement data 245 transferred via the electromagnetic signal 241 and received by the analysis unit 239 and the 3D model of the upper and lower jaw are then used to derive position data 247, for example using a (programmable) processor 249. From the position data 247 a lower border of a lower volume occupied by the lower teeth 123 and an upper border of an upper volume occupied by the upper teeth 103 during the chewing motion are further obtained and will be in more detail described with reference to FIGS. 6, 7 and 8.

Figure 3:
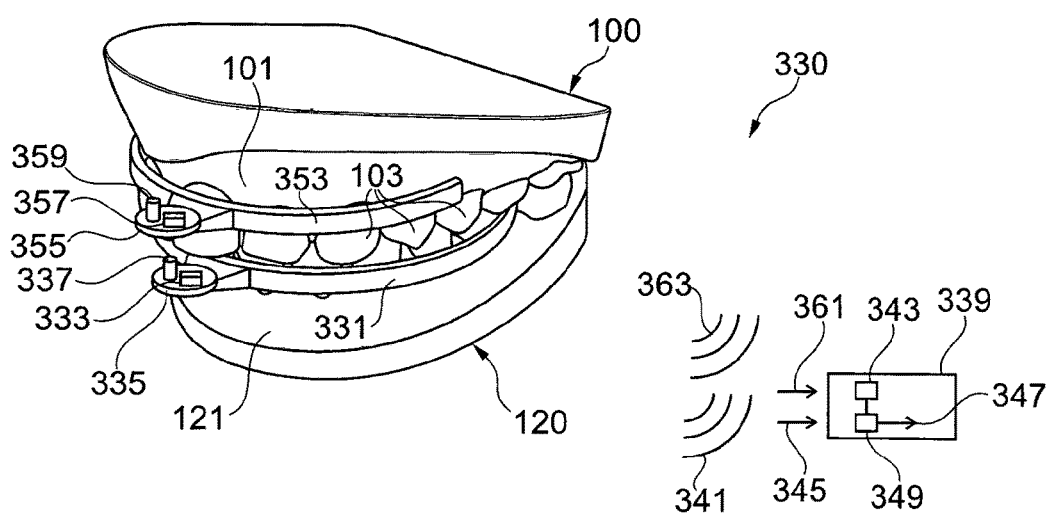
FIG. 3 schematically illustrates in a perspective view a motion sensor of an arrangement for tracking a movement according to an embodiment of the present invention, as installed at an upper and a lower jaw.

FIG. 3 schematically illustrates an arrangement 330 for tracking a movement according to a further embodiment of the present invention. At the lower jaw 120 a lower mounting structure 331 has been mounted at an outer surface of the lower teeth 123 in a fixed position relative to the lower jaw 120. Thereby, the lower mounting structure 331 comprises a clip or a strap which has elastic properties and which can engage around outer surfaces of the lower teeth 123. At a dental front side the lower mounting structure 331 has mounted (fixed thereto) a lower motion sensor system 333 which may be similarly configured as the lower motion sensor system 233 illustrated in FIG. 2. Again, the lower motion sensor system 333 comprises a position sensor 335 and a data transmission unit 337.

Different from the arrangement 230 for tracking a movement as illustrated in FIG. 2, the arrangement 330 for tracking the movement as illustrated in FIG. 3 also comprises an upper mounting structure 353 which is clipped and thereby fixedly mounted at outside surfaces of the upper teeth 103 and also partially engaging with and contacting the upper teethridge 101. Also at a front side portion the upper mounting structure 353 has mounted an upper motion sensor system 355 also having a position sensor 357 and a data transmission unit 359. Thereby, the lower motion sensor system 333 and the upper motion sensor system 355 may essentially be configured similarly or even in an identical manner.

The lower motion sensor system 333 transmits, during a chewing motion, the measurement data 345 via the Bluetooth signal 341 to the analysis unit 339. Additionally, either simultaneously or successively, also the upper motion sensor system 355 transmits measurement data 361 via the Bluetooth signal 363 to the analysis unit 339. The analysis unit 339 may similarly be configured as the analysis unit 239 illustrated in FIG. 2 except that the analysis unit 339 is adapted to process the measurement data 345 received from the lower motion sensor system 333 as well as the measurement data 361 transmitted from the upper motion sensor system 355, in order to obtain, in particular also depending on a 3D model, the position data 347 describing the relative motion of the upper jaw 100 and the lower jaw 120.

The mounting structures 331, 353 represent examples of para-occlusal fixation equipment.

Figure 4:
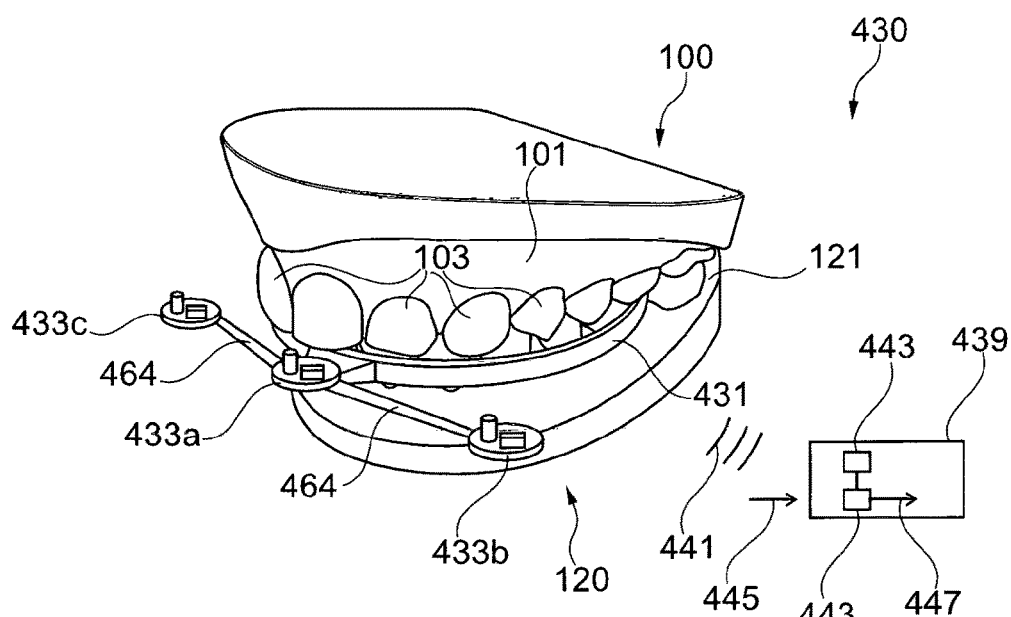
FIG. 4 schematically illustrates a lower motion sensor system of an arrangement for tracking a movement according to another embodiment of the present invention.

FIG. 4 schematically illustrates an arrangement 430 for tracking a movement according to another embodiment of the present invention. The arrangement 430 comprises a lower mounting structure 431 which is similarly configured as the lower mounting structure 331 illustrated in FIG. 3. Different from the lower mounting structure 331 illustrated in FIG. 3, the lower mounting structure 431 illustrated in FIG. 4 has three lower motion sensor systems 433a, 433b and 433c mounted thereon (in a fixed manner). These three lower motion sensor systems 433a, 433b, 433c may be similarly or even identically configured. The lower motion sensor system 433a is located at a central frontal position, while the lower motion sensor systems 433b and 433c are spaced apart from the central position by respective bars 464 extending from the central position to the right and to the left. All three lower motion sensor systems 433a, 433b and 433c may acquire, during a chewing motion, measurement data and may transmit them (as raw data or as preprocessed data) separately or in a combined manner to the analysis module 439 via Bluetooth signal 441 as measurement data 445. The arrangement 430 may further, optionally, comprise an upper motion sensor system 355 and an associated mounting structure 353 as illustrated in FIG. 3.

Figure 5:
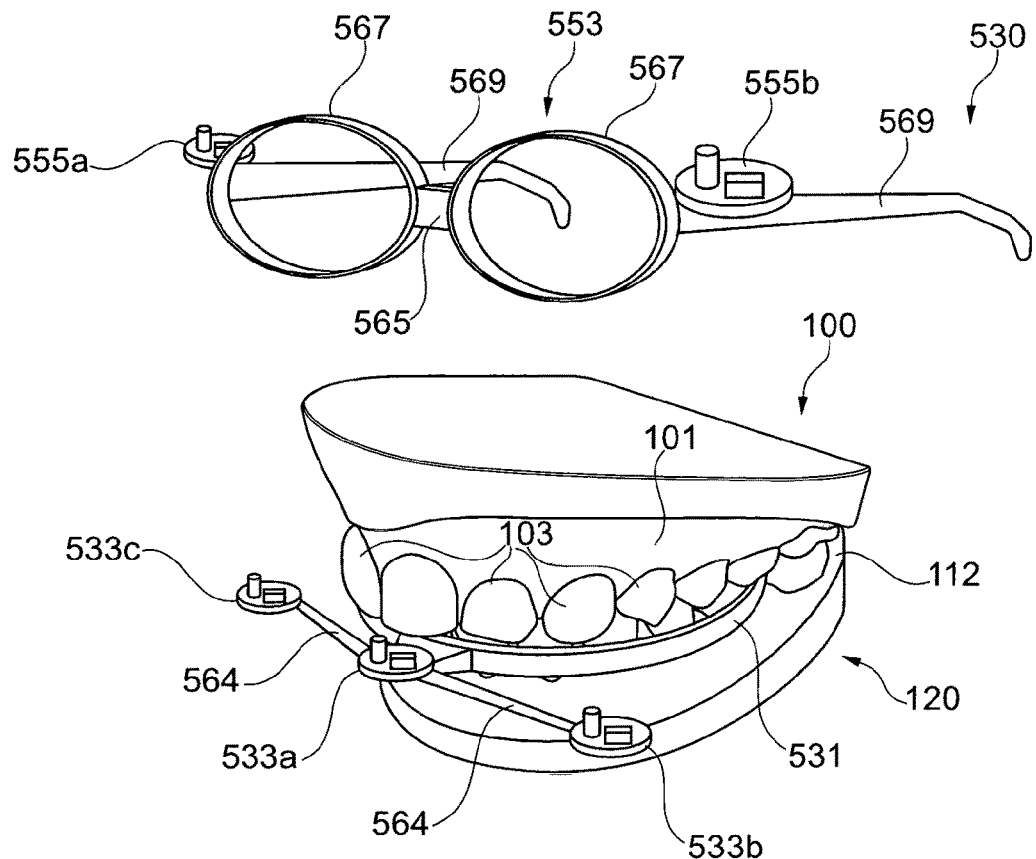
FIG. 5 illustrates equipment of an arrangement for tracking a movement according to an embodiment of the present invention.

FIG. 5 schematically illustrates a tracking system 530 according to a still further embodiment of the present invention. The arrangement 530 comprises the same lower motion sensor system 433 and lower mounting structure 431 as is illustrated and described with reference to FIG. 4.

Differing from the arrangement 330 illustrated in FIG. 3, the arrangement 530 illustrated in FIG. 5 comprises the upper mounting structure 553 which is here configured similar to a frame for glasses. The frame for glasses or upper mounting structure 553 comprises a nose support portion 565 configured to be supported by a nose of the patient to be treated (not explicitly illustrated). The mounting structure 553 further comprises glass frames 567 attached to both sides of the nose support structure or nose pad 565 and furthermore two temples 569 having a curved end to be put over two ears of the patient. On both or one of the temples 569 or bars the mounting structure 553 has fixedly mounted at least one upper motion sensor system 555a, 555b which may be similarly or identically configured as the upper motion sensor system 355 illustrated in FIG. 3. The mounting structure 553 can further be fixed to the skull of the patient using a rubber band or the like.

Figure 6A:
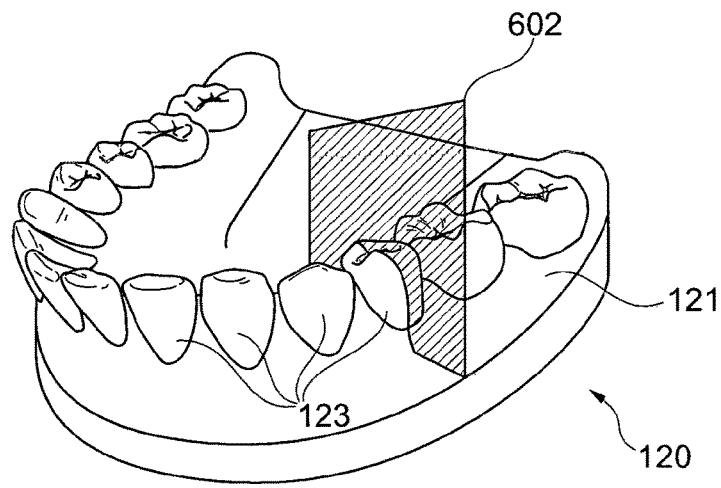
FIGS. 6A, 6B, 6C, 6D and 6E schematically illustrate the acquisition of different states during a chewing motion as performed by an arrangement for tracking a movement according to an embodiment of the present invention.
Figure 6B:
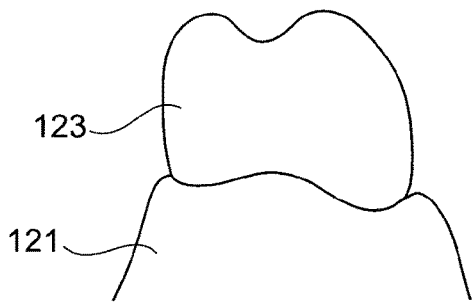
Figure 6C:
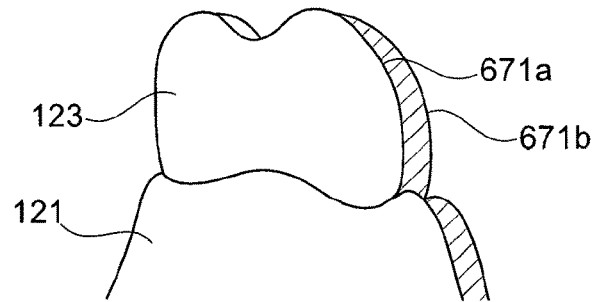
Figures 6D, 6E:
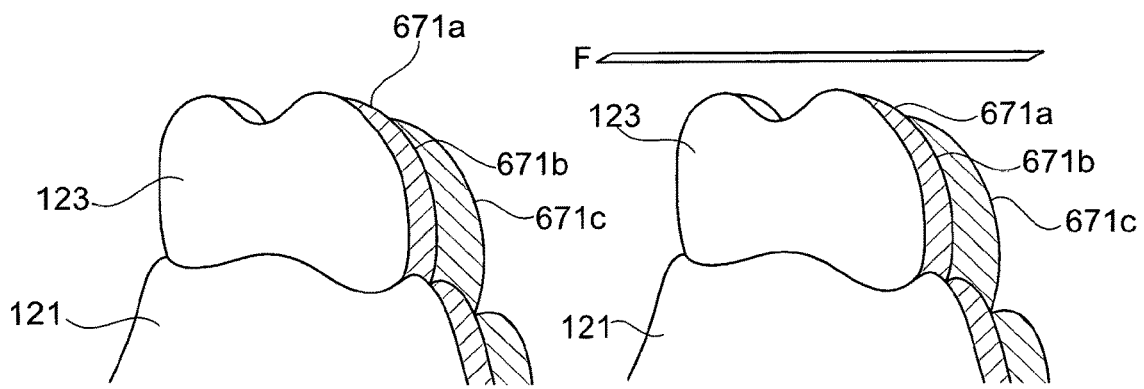

FIGS. 6A to 6E schematically illustrate different states of one tooth 123 during a chewing motion. FIG. 6A schematically illustrates a plane 602 running through the tooth 123 which plane 602 is illustrated in FIG. 6B to 6E in different time instances during a chewing motion. In FIG. 6B, for example the reference state, as for example illustrated in FIG. 1, is illustrated. Then, the patient is asked to perform a chewing motion and the state illustrated in FIGS. 6C, 6D and 6E are acquired using an arrangement 230, 330, 430 or 530 as illustrated in FIG. 2, 3, 4 or 5. As can be appreciated from FIGS. 6B to 6E, the tooth 123 follows a trajectory including a side translation and a vertical translation, such that the edge of the tooth 123 or the outline of the tooth 123 exhibits the shapes 671a, 671b, 671c.

Figures 7A, 7B:
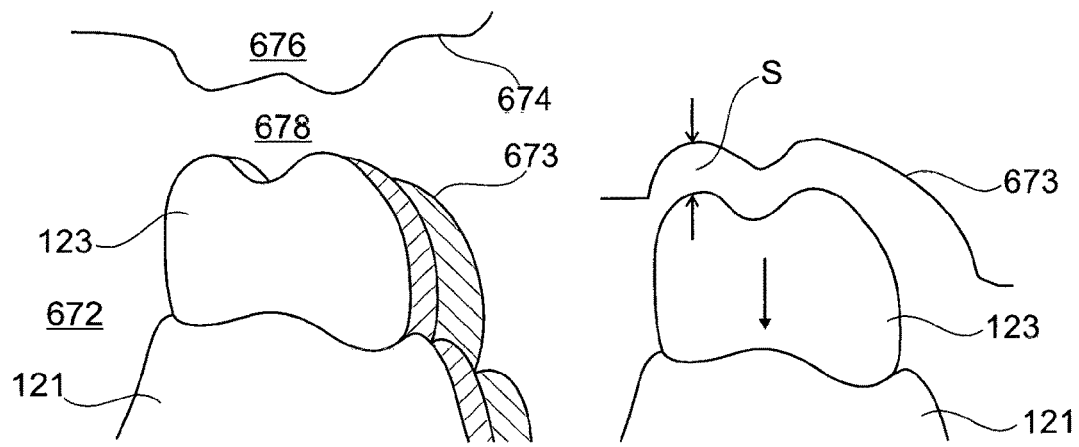
FIGS. 7A and 7B illustrate in a cross-sectional view a determination or modification of a lower border considered in embodiments according to the present invention.

The maximally occupied space by the tooth 123 during the chewing motion is limited by a so-called lower border 673 as illustrated in FIG. 7A. In a similar manner an upper border 674 may be determined from the relative motion of the upper teeth. The lower border 673 limits the lower volume 672 which represents a volume which is occupied at at least one time instance during the chewing motion by the lower teeth 123. In the space between the lower border 673 and the upper border 674, which space is designated with reference sign 678, no tooth is present during the entire chewing motion.

FIG. 7B illustrates a situation, in which it is desired to lower a lower jaw rotation axis 107, for example to a lowered axis 109 (see FIG. 1). Accordingly, the tooth may digitally be lowered by an amount 's'. The space between the lowered teeth 123 and the lower border 673 may then partly be filled with a dental supplement, for example. The design of the supplement may therefore be defined by establishing the lower border 673.

Figures 8A, 8B:
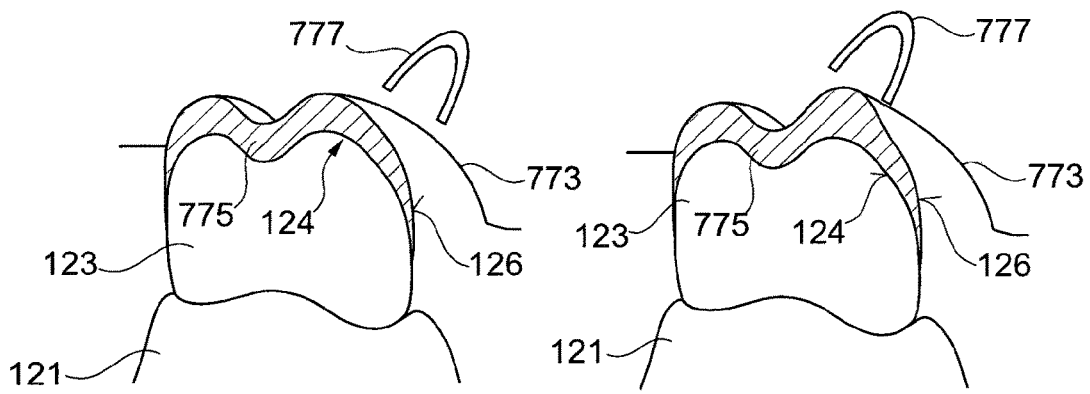
FIGS. 8A and 8B schematically illustrate in a side view or cross-sectional view a method of designing a dental supplement according to embodiments of the present invention.

FIGS. 8A and 8B schematically illustrate a design of a supplement 775 according to an embodiment of the present invention. Again, a lower border 773, such as for example derived as described with reference to FIGS. 6 and 7 may form a basis for designing the dental supplement 775. After lowering the tooth 123, as has been performed according to FIG. 8B, the supplement 775 may, regarding its geometry, be defined by extending the tooth 123 towards the lower border 773, for example using an image modification procedure involving drawing the original surface 124 of the tooth 123 from beyond the lower border 773 using a 'magnet' 777, representing a particular image processing method. The modified upper surface 126 may be restricted to be below the lower border 773 as illustrated in FIG. 8A. In other situations, it may be desirable to even extend the modified upper surface of the teeth beyond the border 773, for example in a case where a redefinition or readjustment of the bite properties is desired, see FIG. 8B.

Figure 9:
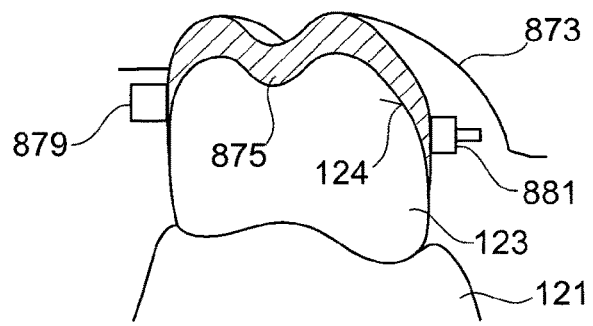
FIG. 9 schematically illustrates a dental supplement in a cross-sectional view as designed and manufactured according to embodiments of the present invention.

FIG. 9 schematically illustrates a supplement 875 which may have been designed and manufactured similarly as described in the previous figures. Additionally, the supplement 875 comprises at least one connector 879 possibly connecting several portions of the dental supplement 875 for increasing the stability and facilitating correct positioning during insertion and adhering it to the tooth 123. Furthermore, for convenient handling by the dentist, at least one handle 881 is provided. The connector 879 as well as the handle 871 may be removed after firmly adhering the dental supplement 875 to the tooth 123.

The supplement 775 or 875 illustrated in FIGS. 8A, 8B, and 9, respectively, may extend over more than one tooth (for example two teeth or three teeth or even more teeth) and can be separated after adhering to the teeth into several supplement portions, each supplement portion being associated with one tooth. Thereby, a handling by the dentist may be simplified. Furthermore, a proper adjustment (regarding positioning and/or orienting) of the supplement over the several teeth may be performed in a more accurate manner. In particular, the connector 879 may additionally strengthen the supplement when extending over several teeth. The supplement may comprise a portion acting as a tooth bridge bridging a tooth gap between teeth. Thereby, different kinds of restoration techniques may be supported.

The invention claimed is:

1. An arrangement for tracking a movement of an upper jaw relative to a lower jaw, the arrangement comprising:
   a lower mounting structure mountable relative to the lower jaw;
   at least one lower motion sensor system mounted at the lower mounting structure; and
   at least one data transmission unit adapted to transmit measurement data from the lower motion sensor system to an analysis unit, wherein the arrangement is configured such that the lower motion sensor system is mountable within the mouth, wherein the lower motion sensor system is arranged in the mouth when the lower mounting structure is mounted to the lower jaw.

2. The arrangement according to claim 1, further comprising:
   an upper mounting structure mountable relative to the upper jaw;
   at least one upper motion sensor system mounted at the upper mounting structure,
   wherein the at least one data transmission unit is further adapted for transmitting measurement data from the upper motion sensor system to the analysis unit.

3. The arrangement according to claim 2, wherein the lower motion sensor system and/or the upper motion sensor system are configured as position sensors with an accuracy of between 0.001 mm and 0.5 mm.

4. The arrangement according to claim 3, wherein the upper motion sensor and/or the lower motion sensor is configured as a Micro-Electro-Mechanical System.

5. The arrangement according to claim 2, wherein the upper motion sensor system and/or the lower motion sensor system comprises:
   an accelerometer and/or a gyroscope;
   a microcontroller;
   an electronic storage; and
   a battery.

6. The arrangement according to claim 5, wherein the accelerometer and/or the gyroscope comprise a 6-axis or 9-axis combo sensor.

7. The arrangement according to claim 2, wherein the upper and/or lower mounting structure comprises a frame and/or a clamp and/or a strap adapted for paraocclusal mounting, such that a chewing motion is unimpaired.

8. The arrangement according to claim 2, further comprising:
   an analysis module for analysing the measurement data acquired during a chewing motion,
   wherein the analysis module comprises an electronic storage for storing a 3D model of the upper jaw including plural upper teeth and the lower jaw including plural lower teeth,
   wherein the analysis module is adapted
      to derive, from the measurement data transmitted from the lower motion sensor system and/or the upper motion sensor system, position data representing positions of the upper teeth/jaw relative to position of the lower teeth/jaw.

9. The arrangement according to claim 8, wherein the analysis module is further adapted
   to obtain, from the position data and/or the 3D model,
      a lower border of a lower volume occupied by the lower teeth during the chewing motion
      an upper border of an upper volume occupied by the upper teeth during the chewing motion.

10. The arrangement according to claim 9, wherein the analysis module is further adapted
    to define a location and/or geometry of a supplement for at least one tooth of the lower teeth and/or the upper teeth based on the upper border and the lower border, the supplement to be added to the at least one tooth for achieving a desired bite adjustment or chewing motion.

11. The arrangement according to claim 8, wherein the analysis module is further adapted
    to define a location and/or geometry of an excess portion of at least one tooth of the lower teeth and/or the upper teeth based on the upper border and the lower border, the excess portion interfering with a desired bite adjustment or chewing motion.

12. The arrangement according to claim 8, wherein the position data is applicable for deriving a jaw movement and/or a jaw movement axis.

13. The arrangement according to claim 1, wherein the at least one data transmission unit comprises:
    a wireless data interface, for transmitting data, including measurement data and/or data derived from the measurement data.

14. The arrangement according to claim 13, wherein the wireless data interface is compatible with Bluetooth technology.

15. The arrangement according to claim 1, wherein the at least one lower motion sensor system comprises several lower motion sensor systems whose measurement data are combinable for obtaining higher accuracy.

16. The arrangement according to claim 1, wherein, when the lower mounting structure is mounted to the lower jaw, the entire lower mounting structure and the data transmission unit are arranged within the mouth.

17. The arrangement according to claim 1, wherein the lower mounting structure does not protrude from the mouth, when the lower mounting structure is mounted to the lower jaw.

18. A method for tracking a movement of an upper jaw relative to a lower jaw, the method comprising:
    affixing a lower mounting structure relative to the lower jaw, wherein at least one lower motion sensor system is mounted at the lower mounting structure, wherein the lower mounting structure and the at least one lower motion sensor system are part of an arrangement according to claim 1; and
    transmitting measurement data from the lower motion sensor system to an analysis unit, the measurement data being acquired during a chewing motion.

19. The method according to claim 18, further comprising:
    positioning and/or orienting the lower jaw and the upper jaw to be in a reference relative position/orientation before or after the acquiring the measurement data during the chewing motion.

20. A method for designing a supplement for at least one tooth, comprising:
    performing a method for tracking a movement of an upper jaw relative to a lower jaw according to claim 18;
    deriving, from the measurement data, position data representing positions of the upper teeth/jaw relative to positions of the lower teeth/jaw;
    determining, from the position data and a 3D model of the upper jaw and the lower jaw, a lower border of a lower volume occupied by the lower teeth during the chewing motion an upper border of an upper volume occupied by the upper teeth during the chewing motion; and defining a location and/or geometry of the supplement based on the lower border and the upper border.

21. A method for manufacturing a supplement for at least one tooth, comprising:

performing a method for designing the supplement for the at least one tooth according to claim 20; and manufacturing, using a 3D printer, the supplement according to the defined geometry of the supplement.

22. An arrangement for tracking a movement of an upper jaw relative to a lower jaw, the arrangement comprising:

a lower mounting structure mountable relative to the lower jaw;

at least one lower motion sensor system mounted at the lower mounting structure, wherein the lower motion sensor system comprises an accelerometer and/or gyroscope, a microcontroller, an electronic storage and a battery; and at least one data transmission unit adapted to transmit measurement data from the lower motion sensor system to an analysis unit, wherein the arrangement is configured such that the lower motion sensor system is mountable within the mouth, wherein the lower motion sensor system is arranged in the mouth when the lower mounting structure is mounted to the lower jaw, wherein the lower mounting structure does not protrude from the mouth, when the lower mounting structure is mounted to the lower jaw.

* * * * *